United States Patent
Li et al.

(10) Patent No.: US 9,730,604 B2
(45) Date of Patent: Aug. 15, 2017

(54) METHODS FOR DETECTING ATRIAL TACHYARRHYTHMIA IN IMPLANTABLE DEVICES WITHOUT DEDICATED ATRIAL SENSING

(71) Applicant: Cardiac Pacemakers, Inc., St. Paul, MN (US)

(72) Inventors: Dan Li, Lexington, MA (US); David L. Perschbacher, Coon Rapids, MN (US); Yanting Dong, Lexington, KY (US); Julie Stephenson, Princeton, NJ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/007,637

(22) Filed: Jan. 27, 2016

(65) Prior Publication Data

US 2016/0135707 A1 May 19, 2016

Related U.S. Application Data

(63) Continuation of application No. 12/754,932, filed on Apr. 6, 2010, now Pat. No. 9,510,764.

(Continued)

(51) Int. Cl.
*A61B 5/0464* (2006.01)
*A61B 5/00* (2006.01)
(Continued)

(52) U.S. Cl.
CPC .......... *A61B 5/0464* (2013.01); *A61B 5/0006* (2013.01); *A61B 5/0031* (2013.01);
(Continued)

(58) Field of Classification Search
CPC ... A61B 5/0006; A61B 5/0031; A61B 5/0464; A61N 1/36592; A61N 1/3624
(Continued)

(56) References Cited

U.S. PATENT DOCUMENTS 5,249,699 A 10/1993 Williams
5,379,776 A * 1/1995 Murphy ............... A61N 1/3622
600/515

(Continued)

OTHER PUBLICATIONS

"U.S. Appl. No. 12/754,932, Decision on Pre-Appeal Brief mailed Jul. 1, 2015", 2 pgs.
(Continued)

*Primary Examiner* — Alyssa M Alter
(74) *Attorney, Agent, or Firm* — Schwegman Lundberg & Woessner, P.A.

(57) ABSTRACT

An apparatus comprises an implantable cardiac signal sensing circuit configured to provide a sensed depolarization signal from a ventricle and a processor. The processor includes a signal analyzer module and a tachyarrhythmia discrimination module. The signal analyzer module is configured to determine a measure of stability of ventricular (V-V) depolarization intervals using the depolarization signal, and determine a rate of change of the measure of stability. The tachyarrhythmia discrimination module is configured to detect an episode of tachyarrhythmia using the depolarization signal, determine whether the detected tachyarrhythmia is indicative of atrial tachyarrhythmia using the determined rate of change, and provide the determination to a user or process.

12 Claims, 5 Drawing Sheets

Related U.S. Application Data

(60) Provisional application No. 61/171,739, filed on Apr. 22, 2009.

(51) Int. Cl.
*A61B 5/04* (2006.01)
*A61N 1/362* (2006.01)
*A61N 1/365* (2006.01)

(52) U.S. Cl.
CPC .......... *A61B 5/04012* (2013.01); *A61B 5/686* (2013.01); *A61N 1/3624* (2013.01); *A61N 1/36592* (2013.01)

(58) Field of Classification Search
USPC ........................................................ 600/518
See application file for complete search history.

(56) References Cited

U.S. PATENT DOCUMENTS

| | | | |
|---|---|---|---|
| 5,755,736 A | 5/1998 | Gillberg et al. |
| 5,759,196 A | 6/1998 | Hess et al. |
| 5,840,079 A | 11/1998 | Warman et al. |
| 5,968,079 A | 10/1999 | Warman et al. |
| 5,991,657 A | 11/1999 | Kim |
| 6,047,210 A | 4/2000 | Kim et al. |
| 6,052,620 A | 4/2000 | Gillberg et al. |
| 6,091,988 A | 7/2000 | Warman et al. |
| 6,249,699 B1 | 6/2001 | Kim |
| 6,272,380 B1 | 8/2001 | Warman et al. |
| 6,330,477 B1 | 12/2001 | Casavant |
| 6,434,424 B1 | 8/2002 | Igel et al. |
| 6,493,579 B1 | 12/2002 | Gilkerson et al. |
| 6,571,122 B2 | 5/2003 | Schroeppel et al. |
| 6,584,350 B2 | 6/2003 | Kim et al. |
| 6,658,286 B2 | 12/2003 | Seim |
| 6,704,597 B1 | 3/2004 | Ware et al. |
| 6,829,504 B1 | 12/2004 | Chen et al. |
| 7,050,852 B2 | 5/2006 | Zhu et al. |
| 7,058,448 B2 | 6/2006 | Noren |
| 7,110,811 B2 | 9/2006 | Wagner et al. |
| 7,142,918 B2 | 11/2006 | Stahmann et al. |
| 7,203,539 B2 | 4/2007 | Ware et al. |
| 7,209,785 B2 | 4/2007 | Kim et al. |
| 7,212,860 B2 | 5/2007 | Stahmann et al. |
| 7,272,438 B2 | 9/2007 | Kroll et al. |
| 7,328,063 B2 | 2/2008 | Zhang et al. |
| 7,398,123 B1 | 7/2008 | Levine |
| 7,537,569 B2 | 5/2009 | Sarkar et al. |
| 7,580,740 B2 | 8/2009 | Kim et al. |
| 2006/0074330 A1 | 4/2006 | Smith et al. |
| 2007/0219456 A1 | 9/2007 | Thompson |
| 2008/0114258 A1 | 5/2008 | Zhang et al. |
| 2009/0054943 A1 | 2/2009 | Qu et al. |
| 2009/0163966 A1 | 6/2009 | Perschbacher et al. |
| 2009/0299425 A1 | 12/2009 | Kim et al. |
| 2009/0306486 A1 | 12/2009 | Li et al. |
| 2010/0274149 A1 | 10/2010 | Li et al. |

OTHER PUBLICATIONS

"U.S. Appl. No. 12/754,932, Final Office Action mailed Oct. 22, 2014", 8 pgs.

"U.S. Appl. No. 12/754,932, Non Final Office Action mailed Mar. 17, 2014", 7 pgs.

"U.S. Appl. No. 12/754,932, Non Final Office Action mailed Mar. 25, 2013", 7 pgs.

"U.S. Appl. No. 12/754,932, Notice of Allowance mailed Oct. 13, 2015", 7 pgs.

"U.S. Appl. No. 12/754,932, Pre-Appeal Brief Request filed Dec. 9, 2014", 5 pgs.

"U.S. Appl. No. 12/754,932, Response filed May 21, 2013 to Non Final Office Action mailed Mar. 25, 2013", 12 pgs.

"U.S. Appl. No. 12/754,932, Response filed Jun. 17, 2014 to Non Final Office Action mailed Mar. 17, 2014", 12 pgs.

"U.S. Appl. No. 12/754,932, Response filed Nov. 9, 2012 to Restriction Requirement mailed Oct. 26, 2012", 9 pgs.

"U.S. Appl. No. 12/754,932, Restriction Requirement mailed Oct. 26, 2012", 6 pgs.

Garcia-Alberola, A., et al., "RR interval variability in irregular monomorphic ventricular tachycardia and atrial fibrillation.", Circulation, 93(2), (Jan. 15, 1996), 295-300.

Swerdlow, C. D, et al., "Advanced ICD Troubleshooting: Part I", PACE, vol. 28, [Online]. Retrieved from the Internet: <http://www.medscape.com/viewarticle/520588_print>, (Jan. 9, 2006), 1322-1346.

Swerdlow, C. D, et al., "Discrimination of ventricular tachycardia from sinus tachycardia and atrial fibrillation in a tiered-therapy cardioverter-defibrillator.", J Am Coll Cardiol., 23(6), (May 1994), 1342-55.

Swerdlow, C. D, et al., "Underdetection of ventricular tachycardia by algorithms to enhance specificity in a tiered-therapy cardioverter-defibrillator.", J Am Coll Cardiol., 24(2), (Aug. 1994), 416-24.

Volosin, K. J, et al., "Spontaneous changes in ventricular tachycardia cycle length.", J Am Coll Cardiol., 17(2), (Feb. 1991), 409-14.

\* cited by examiner

METHODS FOR DETECTING ATRIAL TACHYARRHYTHMIA IN IMPLANTABLE DEVICES WITHOUT DEDICATED ATRIAL SENSING

CROSS REFERENCE TO RELATED APPLICATION

This application is a division of U.S. application Ser. No. 12/754,932, filed Apr. 6, 2010, which claims the benefit of U.S. Provisional Application No. 61/171,739, filed on Apr. 22, 2009, under 35 U.S.C. §119(e), which is hereby incorporated by reference.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, ventricular tachyarrhythmia can be terminated with high-energy shock therapy delivered with an ICD. Cardioversion/defibrillation therapy can cause patient discomfort and consumes a relatively large amount of battery power which may lead to a shortened useful device lifetime. Some ICDs are single chamber devices that sense cardiac signals and deliver therapy to a single heart chamber (e.g., the right ventricle). However, ICD patients may develop atrial arrhythmias. Atrial tachyarrhythmia includes atrial fibrillation (AF) and atrial tachycardia (AT). Atrial tachyarrhythmia with a fast ventricular response (e.g., resulting in a fast ventricular rate) is often a cause of inappropriate shocks by an ICD.

Overview

This document relates generally to systems, devices, and methods for monitoring cardiac electrophysiological parameters of a patient or subject. Episodes of atrial and ventricular tachyarrhythmia are also monitored.

In example 1, an apparatus includes an implantable cardiac signal sensing circuit configured to provide a sensed depolarization signal from a ventricle and a processor communicatively coupled to the cardiac signal sensing circuit. The processor includes a signal analyzer module and a tachyarrhythmia discrimination module. The signal analyzer module is configured to determine a measure of stability of ventricular (V-V) depolarization intervals using the depolarization signal, and determine a rate of change of the measure of stability. The tachyarrhythmia discrimination module is configured to detect an episode of tachyarrhythmia using the depolarization signal, determine whether the detected tachyarrhythmia is indicative of atrial tachyarrhythmia using the determined rate of change, and provide the determination to a user or process.

In example 2, the tachyarrhythmia discrimination module of example 1 is optionally configured to classify the detected tachyarrhythmia as atrial tachyarrhythmia when the rate of change of the measure of stability exceeds an atrial tachyarrhythmia rate of change detection threshold.

In example 3, the tachyarrhythmia discrimination module of examples 1 and 2 is optionally configured to classify the detected tachyarrhythmia as ventricular tachyarrhythmia when the rate of change of the measure of stability is greater than a ventricular tachyarrhythmia rate of change detection threshold and is less than the atrial tachyarrhythmia rate of change detection threshold.

In example 4, the signal analyzer module of examples 1-3 is optionally configured to determine a rate of change of the measure of stability when a ventricular depolarization rate or interval satisfies a specified threshold rate or threshold interval value. The tachyarrhythmia discrimination module is optionally configured to classify the detected tachyarrhythmia according to the rate of change of the measure of stability when the ventricular rate or interval satisfies the specified threshold value, and classify the detected tachyarrhythmia according to the measure of stability otherwise.

In example 5, the apparatus of examples 1-4 optionally includes a memory communicatively coupled to the processor and configured to a store a signal morphology template, and a far-field sensing channel configured to provide a far-field atrial and ventricular signal using an electrode location that is outside of an atrium or ventricle. The tachyarrhythmia discrimination module is optionally configured to, upon determining the detected tachyarrhythmia is atrial tachyarrhythmia, initiate sensing of the far-field signal, initiate a comparison of a morphology of the sensed far-field signal to a stored morphology template by the signal analyzer module, and confirm the classification as atrial tachyarrhythmia using the morphology comparison.

In example 6, the signal analyzer module of example 5 is optionally configured to calculate a measure of similarity between a segment of the far-field signal and the morphology template which is representative of normal sinus rhythm, and calculate a central tendency of the measure of similarity and a variance of the measure of similarity. The tachyarrhythmia discrimination module is optionally configured to confirm the classification as atrial tachyarrhythmia when the central tendency of the measure of similarity is above a central tendency threshold and the variance of the measure of similarity is within a variance range.

In example 7, the stored morphology template of examples 5 and 6 is optionally associated with atrial tachyarrhythmia.

In example 8, apparatus of examples 1-7 optionally includes a memory and a communication circuit communicatively coupled to the processor. The communication circuit is configured to communicate information wirelessly with a second separate device. The tachyarrhythmia discrimination module is optionally configured to upon classifying the detected tachyarrhythmia as atrial tachyarrhythmia, initiate storage of a segment of the depolarization signal when a duration of the detected tachyarrhythmia exceeds a duration threshold, initiate storage of a histogram of V-V depolarization intervals, wherein the histogram indicates regular and irregular V-V depolarization intervals, and communicate the stored segment and histogram to a second device.

In example 9, the apparatus of examples 1-4 optionally includes a far-field sensing channel configured to provide a far-field atrial signal using an electrode location that is outside of an atrium, a memory communicatively coupled to the processor, and a communication circuit, communicatively coupled to the processor, configured to communicate information wirelessly with a second separate device. The tachyarrhythmia discrimination module is optionally configured to upon classifying the detected tachyarrhythmia as atrial tachyarrhythmia, initiate storage of a segment of the sensed far-field signal when a duration of the detected arrhythmia exceeds a duration threshold, communicate the stored segment to the second device for comparison of a far-field signal morphology to a morphology template, and receive an indication whether the detected tachyarrhythmia is atrial tachyarrhythmia from the second device.

In example 10, a method includes detecting an episode of tachyarrhythmia from a depolarization signal sensed from a ventricle using a dedicated implantable ventricular sensing circuit and in an absence of a dedicated atrial chamber sensing circuit, determining a measure of stability of V-V depolarization intervals using the depolarization signal, determining a rate of change of the measure of stability, classifying the detected tachyarrhythmia as atrial tachyarrhythmia or ventricular tachyarrhythmia using the determined rate of change, and providing the tachyarrhythmia classification to a user or process.

In example 11, the classifying the detected tachyarrhythmia of example 10 optionally includes classifying the detected tachyarrhythmia as atrial tachyarrhythmia when the rate of change of the measure of stability exceeds an atrial tachyarrhythmia rate of change detection threshold.

In example 12, the classifying the detected tachyarrhythmia of examples 10 and 11 optionally includes classifying the detected tachyarrhythmia as ventricular tachyarrhythmia when the rate of change of the measure of stability is greater than a ventricular tachyarrhythmia rate of change detection threshold and is less than the atrial tachyarrhythmia rate of change detection threshold.

In example 13, the determining a rate of change of the measure of stability of examples 10-12 optionally includes determining a rate of change of the measure of stability when the ventricular rate or interval satisfies a threshold rate or interval value. The classifying the detected tachyarrhythmia optionally includes classifying the detected tachyarrhythmia according to the rate of change of the measure of stability when the ventricular rate or interval satisfies the threshold rate or interval value, and classifying the detected tachyarrhythmia according to the measure of stability otherwise.

In example 14, the method of examples 10-13 optionally includes, upon classifying the detected tachyarrhythmia as atrial tachyarrhythmia, sensing a second signal using a far-field sensing channel and comparing a morphology of the second sensed signal to a morphology template. The classifying the tachyarrhythmia optionally includes confirming the classification as atrial tachyarrhythmia using the morphology comparison.

In example 15, the classifying the tachyarrhythmia of example 14 optionally includes calculating a measure of similarity between a segment of the second signal and the morphology template, wherein the morphology template is representative of normal sinus rhythm, calculating a central tendency of the measure of similarity and a variance of the measure of similarity. The confirming the classification optionally includes confirming the classification as atrial tachyarrhythmia when the central tendency of the measure of similarity is above a central tendency threshold and the variance of the measure of similarity is within a variance range.

In example 16, the classifying the tachyarrhythmia of example 14 optionally includes, upon classifying the detected tachyarrhythmia as atrial tachyarrhythmia, storing a segment of the second signal when a duration of the detected arrhythmia exceeds a duration threshold. The comparing a morphology optionally includes communicating the stored segment from a first implantable medical device to a second device and comparing the morphology of the second sensed signal to the morphology template using the second device, and the classification optionally includes confirming the classification as atrial tachyarrhythmia using the morphology comparison by the second device.

In example 17, the comparing a morphology of the second signal of examples 14-16 optionally includes comparing a morphology of the second sensed signal to a morphology template associated with atrial tachyarrhythmia.

In example 18, the method of examples 10-17 optionally includes, upon classifying the detected tachyarrhythmia as atrial tachyarrhythmia, storing a segment of the depolarization signal when a duration of the detected tachyarrhythmia exceeds a duration threshold, storing a histogram of V-V depolarization intervals, wherein the histogram indicates regular and irregular V-V depolarization intervals, and communicating the stored segment and histogram from an implantable medical device to a second device.

In example 19, an apparatus includes an implantable cardiac signal sensing circuit, configured to provide a sensed depolarization signal from a ventricle, and a processor. The processor is communicatively coupled to the cardiac signal sensing circuit and includes a signal analyzer module configured to measure V-V depolarization intervals and a tachyarrhythmia discrimination module configured to detect an episode of tachyarrhythmia using the measured V-V depolarization intervals, detect a sudden presence of long and short V-V depolarization intervals, classify the detected tachyarrhythmia as atrial tachyarrhythmia or ventricular tachyarrhythmia using a detected pattern of long and short V-V depolarization intervals, and provide the tachyarrhythmia classification to a user or process.

In example 20, the apparatus of example 19 optionally includes a memory communicatively coupled to the processor and configured to a store a signal morphology template and a far-field sensing channel configured to provide a far-field atrial and ventricular signal using an electrode location that is outside of an atrium or ventricle. The tachyarrhythmia discrimination module is optionally configured to, upon classifying the detected tachyarrhythmia as atrial tachyarrhythmia, initiate sensing of the far-field signal, and initiate a comparison a morphology of the far-field signal to a stored morphology template by the signal analyzer module, and confirm the classification as atrial tachyarrhythmia using the morphology comparison.

In example 21, the signal analyzer module of examples 19 and 20 is optionally configured to calculate a measure of similarity between a segment of the far-field signal and the morphology template, wherein the stored morphology template is representative of normal sinus rhythm, and calculate a central tendency of the measure of similarity and a variance of the measure of similarity. The tachyarrhythmia discrimination module is optionally configured to confirm the classification as atrial tachyarrhythmia when the central tendency of the measure of similarity is above a central tendency threshold, the variance of the measure of similarity is within a variance range, and the depolarization rate or interval satisfies a rate or interval detection threshold.

In example 22, the apparatus of examples 19-21 optionally includes a memory and a communication circuit communicatively coupled to the processor. The communication circuit is configured to communicate information wirelessly with a second separate device. The tachyarrhythmia discrimination module is optionally configured to, upon classifying the detected tachyarrhythmia as atrial tachyarrhythmia, initiate storage of a segment of the depolarization signal when a duration of the detected arrhythmia exceeds a duration threshold, initiate storage of a histogram of V-V depolarization intervals, wherein the histogram indicates regular and irregular V-V depolarization intervals, and communicate the stored segment and histogram from an implantable medical device to a second device.

In example 23, a method includes detecting an episode of tachyarrhythmia using a depolarization signal sensed from a ventricle in an absence of a dedicated atrial chamber sensing circuit, detecting a sudden presence of long and short V-V depolarization intervals using the depolarization signal, classifying the detected tachyarrhythmia as atrial tachyarrhythmia or ventricular tachyarrhythmia using a detected pattern of long and short V-V depolarization intervals, and providing the tachyarrhythmia classification to a user or process.

In example 24, the method of example 23 optionally includes, upon classifying the detected tachyarrhythmia as atrial tachyarrhythmia, sensing a second signal using a far-field sensing channel, and comparing a morphology of the second sensed signal to a morphology template. The classifying the tachyarrhythmia optionally includes confirming the classification as atrial tachyarrhythmia using the morphology comparison.

In example 25, the method of example 23 and 24 optionally includes, upon classifying the detected tachyarrhythmia as atrial tachyarrhythmia, storing a segment of the depolarization signal when a duration of the detected arrhythmia exceeds a duration threshold, storing a histogram of V-V depolarization intervals, wherein the histogram indicates regular and irregular V-V depolarization intervals, and communicating the stored segment and histogram from an implantable medical device to a second device.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved discrimination or classification of tachyarrhythmia by an IMB are described.

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
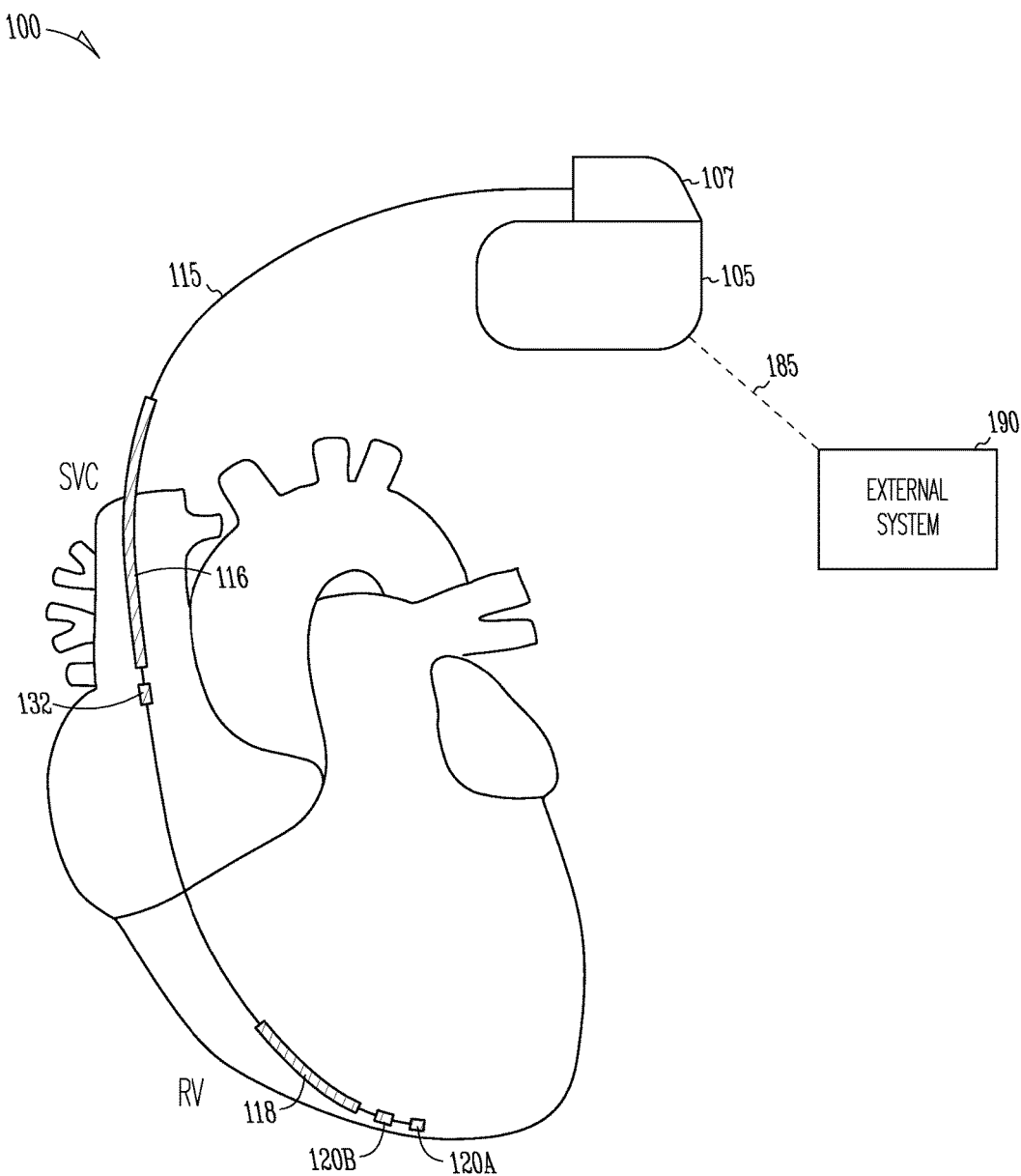
FIG. 1 is an illustration of an example of portions of a system that includes an IMD.

FIG. 1 is an illustration of an example of portions of a system 100 that includes an IMD 105. Examples of IMB 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMB 105 typically includes components that are enclosed in a hermetically-sealed housing sometimes referred to as a canister or "can." The system 100 also typically includes an IMB programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMB 105 allow for sensing an RV electrogram signal representative of RV depolarizations and delivering RV pacing pulses. In some examples, the IMD includes a sense amplifier circuit to provide amplification or filtering of the sensed signal. Sensing and pacing allows the IMB 105 to adjust timing of the heart chamber contractions.

Some IMDs, such as shown in FIG. 1, may not include an electrode for sensing electrical activity in an atrium. For example, the IMB 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis). The absence of sensing intrinsic atrial depolarizations (P-waves) may make arrhythmia detection perform less well than a dual chamber ICD (e.g., an ICD including a lead for placement in an atrium and a lead for placement in a ventricle).

Lack of atrial sensing makes it difficult for a clinician to retrospectively diagnose atrial tachyarrhythmia such as atrial fibrillation (AF) and atrial tachycardia (AT). Yet, AF/AT detection has important diagnostic value. The time that a patient spends in AF is sometimes called an AF burden. A device estimate of the AF burden is useful to a clinician to determine which anti-arrhythmic therapy or therapies to use, or which anticoagulant therapy or therapies to prescribe. Detection of AF is also useful for discriminating between AF and VT. And, as set forth above, occurrences of AT or AF with a fast ventricular response is a major cause of inappropriate shocks.

Figure 2:
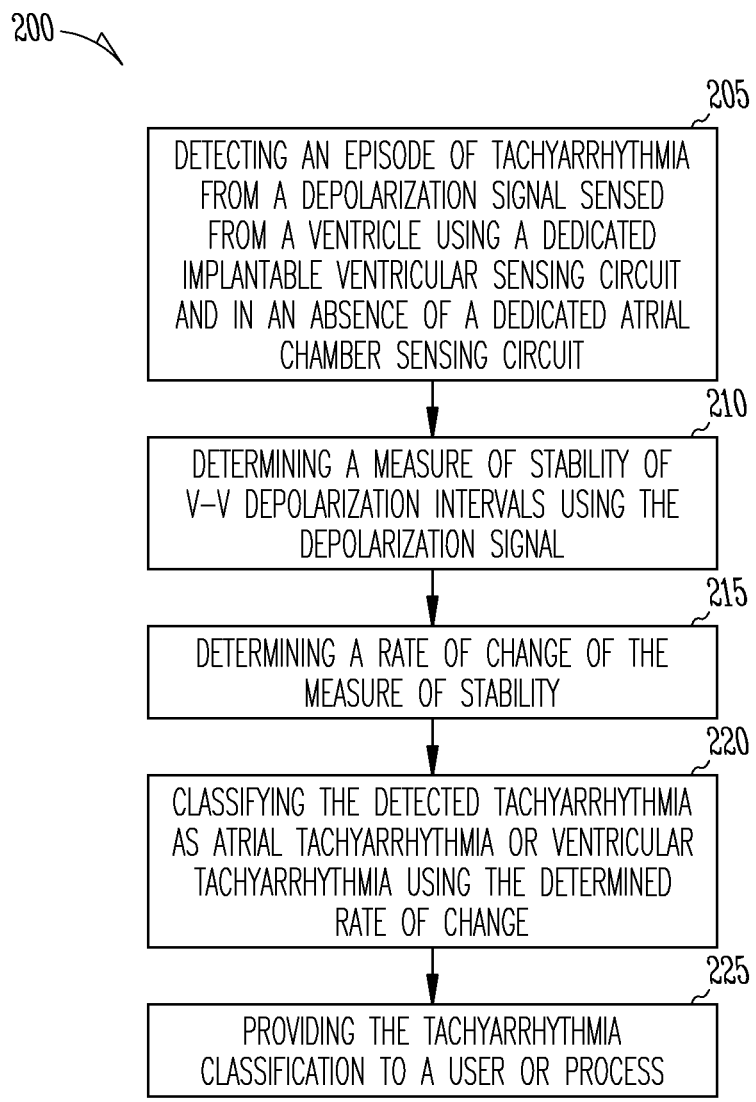
FIG. 2 is a flow diagram of an example of a method of detecting and classifying atrial tachyarrhythmia using an IMD.

FIG. 2 is a flow diagram of an example of a method 200 of detecting and classifying atrial tachyarrhythmia using an IMB that does not have dedicated atrial sensing circuits.

At block 205, an episode of tachyarrhythmia is detected using a device such as an IMB. The tachyarrhythmia is detected from a cardiac depolarization signal sensed from a ventricle using a dedicated implantable ventricular sensing circuit and in an absence of a dedicated atrial chamber sensing circuit. For instance, the depolarization signal may be sensed using bipolar electrodes 120A and 120B and a sense amplifier as discussed above in regard to FIG. 1, or the depolarization signal may be sensed as part of a wireless ECG which uses electrodes formed on the IMB housing. In certain examples, the device senses cardiac depolarization signals and detects tachyarrhythmia by detecting a depolarization rate that exceeds a tachyarrhythmia detection rate threshold.

At block 210, a measure of stability of ventricular depolarization (V-V) intervals is determined using the depolarization signal. In certain examples, the V-V intervals are measured by detecting R-waves in the depolarization signal and measuring the intervals between R-waves (i.e., RR intervals). R-waves of the QRS wave complex are indicative of depolarization of the ventricles.

The measure of stability indicates the variability of V-V interval differences. In some examples of a stability measurement, pair-wise differences of V-V intervals are calculated (ΔV-V). When a tachyarrhythmia episode is detected, the stability measurement is initialized using an average of a specified number (e.g., four) V-V interval differences. The stability is then calculated on the fly during the episode. In certain examples, when a new V-V interval is detected, a current difference in the V-V interval is calculated and the stability measurement is calculated as the current difference minus the average of the previous differences.

In certain examples, a weighted stability calculation is used to assess stability. The stability measurement (S) is a weighted sum of the previous stability measurement and the current stability measurement. As an illustrative example, if weights of ⅞ and ⅛ are used, then $$(S)_{CURRENT} = \frac{7}{8} * (S)_{PREVIOUS} + \frac{1}{8} * (\Delta V\text{-}V). \tag{1}$$

If the V-V intervals are stable then the V-V intervals are uniform and the differences will approach zero. If the V-V intervals are unstable, then the calculated differences will be greater than zero. The V-V intervals are declared to be unstable if the weighted stability calculation exceeds a predetermined threshold value.

Examples of methods and systems to detect arrhythmia and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

For an atrial tachyarrhythmia such as AF, the V-V intervals will be irregular. Therefore, an atrial tachyarrhythmia is detectable without dedicated atrial sensing circuits by analysis of the V-V intervals. However, tachyarrhythmia discrimination is complicated by the fact that V-V interval instability is not specific to atrial tachyarrhythmia. VT can be irregular as well (e.g., at slower depolarization rates). Also, anti-arrhythmic drugs may cause monomorphic VT (MVT) to become markedly irregular. Thus, VT may be misclassified as atrial tachyarrhythmia (and vice versa) in some circumstances.

A better approach is to monitor a rate of change of V-V interval stability and use the rate of change in discrimination between different forms of tachyarrhythmia. At block 215, a rate of change of the measure of stability is determined. In some examples, the rate of change of stability (dS/dt) is calculated as approximately equal to $$|S_n - S_{n-k}|/k, \tag{3}$$

where n and k are numbers of V-V intervals and k<n.

The rate of change indicates how the stability varies during the detected tachyarrhythmia. For atrial tachyarrhythmia such as AF/AT, the onset of the tachyarrhythmia usually occurs with a sudden change in the V-V stability calculation. Because the stability calculation tends to be near zero for a stable rhythm, the value of the stability calculation will exhibit a sudden increase for AF/AT. For many VTs, the V-V stability calculation gradually changes to a value that indicates instability. Thus, a measure of the change in S with time (or a change over k intervals) is a way to differentiate between AF/AT and VT.

At block 220, the detected tachyarrhythmia is classified as atrial tachyarrhythmia or ventricular tachyarrhythmia using the determined rate of change. At block 225, the tachyarrhythmia classification is provided to a user or process.

Figure 3:
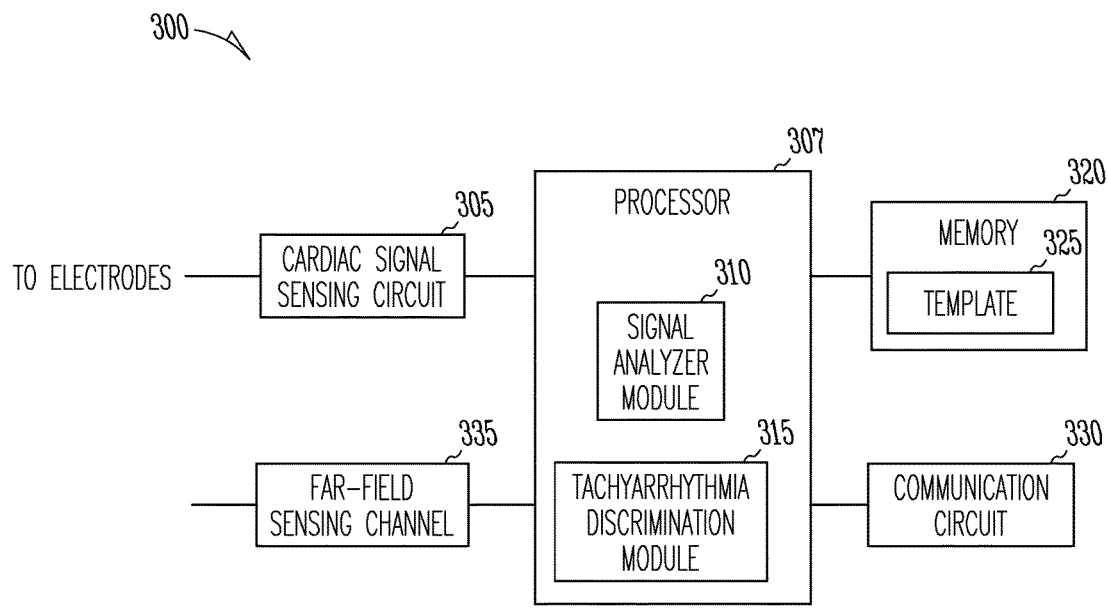
FIG. 3 is a block diagram of portions of an example of an IMD to detect and classify atrial tachyarrhythmia.

FIG. 3 is a block diagram 300 of portions of an example of an IMD 300 to detect and classify atrial tachyarrhythmia. The IMD 300 includes an implantable cardiac signal sensing circuit 305 designed for sensing electrical depolarization signals in a ventricle, such as when the coupled to an electrode shaped and sized to be placed in or near a ventricle of a subject. It is to be noted that the IMD does not include dedicated atrial sensing circuits.

The IMB 300 also includes a processor 307 communicatively coupled to the cardiac signal sensing circuit 305. The processor 307 may be a digital signal processor, ASIC, microprocessor, or other type of processor. Functions and algorithms performed by the processor correspond to modules, which are software, hardware, firmware or any combination thereof. Multiple functions may be performed in one or more modules as desired, and the embodiments described are merely examples. The communicative coupling allows the cardiac signal sensing circuit 305 and the processor 307 to communicate even though there may be intervening circuits between them. For example, the cardiac signal sensing circuit 305 converts sensed cardiac depolarizations into electrical signals and the electrical signals may be quantified for the processor using analog to digital (A/D) converters.

The processor 307 includes a signal analyzer module 310 configured to determine a measure of stability of V-V intervals using the depolarization signal. In some examples, the signal analyzer module 310 determines a weighted stability calculation. The signal analyzer module 310 also determines a rate of change of the measure of stability.

The processor 307 further includes a tachyarrhythmia discrimination module 315 to detect an episode of tachyarrhythmia using the depolarization signal, such as when detecting a depolarization rate that exceeds a tachyarrhythmia detection rate threshold for example. The tachyarrhythmia discrimination module 315 then determines whether the detected tachyarrhythmia is indicative of atrial tachyarrhythmia using the determined rate of change of stability, and provides the determination to a user or process. In some examples, the classification may be used by the IMB 300 to begin an anti-tachyarrhythmia treatment such as anti-tachycardia pacing (ATP) or delivery of an anti-tachyarrhythmia drug. In some examples, the classification is communicated to an external device, such as an IMB programmer or advanced patient management (APM) system.

In some examples, the tachyarrhythmia discrimination module 315 classifies the detected tachyarrhythmia as atrial tachyarrhythmia when the rate of change of the measure of stability exceeds an atrial tachyarrhythmia rate of change detection threshold. In some examples, the tachyarrhythmia discrimination module 315 is configured to classify the detected tachyarrhythmia as ventricular tachyarrhythmia when the rate of change of the measure of stability is greater than a ventricular tachyarrhythmia rate of change detection threshold and is less than the atrial tachyarrhythmia rate of change detection threshold. This reflects the sudden change in stability evident during an onset of atrial tachyarrhythmia versus the gradual change in stability evident during an onset of ventricular tachyarrhythmia.

According to some examples, the tachyarrhythmia discrimination module 315 may use the measure of V-V stability (S) or the rate of change of the measure of stability (dS/dt) to classify the tachyarrhythmia, depending on the detected depolarization rate. Classifying atrial tachyarrhythmia using S may be more reliable at tachyarrhythmia of lower rates while using dS/dt may be more reliable at higher rates.

Thus in some examples, the tachyarrhythmia discrimination module 315 classifies the detected tachyarrhythmia according to the rate of change of the measure of stability when the ventricular rate or interval satisfies the specified threshold value (e.g., >170 beats per minute (bpm)), and classifies the detected tachyarrhythmia according to the measure of stability otherwise (e.g., <170 bpm). The signal analyzer module 310 determines a rate of change of the measure of stability when a ventricular depolarization rate or interval satisfies a specified threshold rate or threshold interval value (e.g., a rate >170 bpm, or a V-V interval <350 ms).

In certain examples, the actual depolarization rate threshold used as the cutoff between the use of S or dS/dt may be made programmable in the device and selected by a clinician. In certain examples, the threshold is an absolute threshold set internally in the IMD and is not programmable. In certain examples, the threshold is dynamic and is a percentage of a running V-V interval average. In certain examples, the threshold is characterized for each individual patient.

In some examples, once the tachyarrhythmia is classified, the IMD 300 gathers statistics about the tachyarrhythmia. In certain examples, the IMD 300 includes a memory 320 and a communication circuit 330 communicatively coupled to the tachyarrhythmia discrimination module 315. The communication circuit 330 communicates information wirelessly with a second separate device. The tachyarrhythmia discrimination module 315 initiates storage of a segment of the depolarization signal upon classifying the detected tachyarrhythmia as atrial tachyarrhythmia and when a duration of the detected tachyarrhythmia exceeds a duration threshold. The tachyarrhythmia discrimination module 315 also initiates storage of a histogram of V-V depolarization intervals. The tachyarrhythmia discrimination module 315 communicates the stored segment and histogram to a second device at a later time. In certain examples, the histogram indicates regular and irregular V-V depolarization intervals in the histogram data.

The IMD 300 may gather other statistics as well, such as a duration of the atrial tachyarrhythmia for example, which may also be communicated to a second device. In certain examples, the second device is part of an advanced patient management (APM) system and is able to communicate wirelessly with the IMD as well as communicate with other devices over a computer network such as the internet or a cellular phone network. In certain examples, a clinician can choose (e.g., by programming) a trigger condition of the statistics that causes the APM system to send out an alert, such as when the duration exceeds a predetermined threshold duration for example.

In some examples, the second device may include a display or may relay the histogram to a third device having a display. The histogram data may be displayed with an indication (e.g., a color code) so the clinician can clearly see the difference in ventricular response when the patient is in atrial tachyarrhythmia. In certain examples, the histogram data is sorted into an AF histogram or an AT histogram. In certain examples, the histogram includes a rate histogram as well as trending of the ventricular rate stability.

According to some examples, once a tachyarrhythmia has been classified, the tachyarrhythmia discrimination module 315 confirms the classification with further analysis.

In certain examples, the IMD 300 uses a signal morphology analysis to confirm the tachyarrhythmia classification. The memory 320 stores a depolarization signal morphology template 325. In certain examples, the signal morphology template is stored in the memory 320 as a data structure. The IMB 300 also includes a far-field sensing channel 335 that provides a sensed far-field atrial and ventricular signal using an electrode location that is outside of an atrium or ventricle. The sensed far-field signal is a more global representation of activity in the atria and ventricles than a near-field signal or signals. In some examples, the far-field sensing channel includes a unipolar sensing vector.

Returning to FIG. 1, in some examples, the unipolar sensing vector includes the coil electrode 116 configured to be placed in or near an SVC and an electrode incorporated into the housing or the header of the IMD 105. In some examples, the unipolar sensing vector includes the distal defibrillation electrode 118 and an electrode incorporated into the housing or the header of the IMD 105. In some examples, the unipolar sensing vector includes a ring electrode 132 configured to be placed in or near the SVC and the electrode incorporated into the housing or the header of the IMB 105. In some examples, the far-field sensing channel 335 is a far-field atrial sensing channel and includes the SVC coil electrode 116 and the SVC ring electrode 132.

The tachyarrhythmia discrimination module 315 initiates sensing of the far-field signal upon determining that the detected tachyarrhythmia is atrial tachyarrhythmia. The tachyarrhythmia discrimination module 315 then initiates a comparison of a morphology of the sensed far-field signal to the stored morphology template 325 by the signal analyzer module 310. The tachyarrhythmia discrimination module 315 confirms the classification as atrial tachyarrhythmia using the morphology comparison.

In some examples, the stored morphology template 325 is associated with atrial tachyarrhythmia. The signal analyzer module 310 calculates a measure of similarity between a segment of the sensed far-field signal and the morphology template 325. If the measure of similarity exceeds a threshold value, the tachyarrhythmia discrimination module 315 deems the detected tachyarrhythmia to be atrial tachyarrhythmia.

In some examples, the stored morphology template 325 is associated with normal sinus rhythm (NSR). The signal analyzer module 310 calculates a measure of similarity between a segment of the sensed far-field signal and the morphology template, and calculates a central tendency of the measure of similarity and a variance of the measure of similarity. The tachyarrhythmia discrimination circuit is confirms the classification as atrial tachyarrhythmia when the central tendency of the measure of similarity is above a central tendency threshold and the variance of the measure of similarity is within a predetermined variance range.

In some examples, at least a portion of the signal processing is performed by a second device. This offloads the processing demand of the signal analyses from the IMD 300 to another device. Upon classifying the detected tachyarrhythmia as atrial tachyarrhythmia and when a duration of the detected arrhythmia exceeds a duration threshold, the tachyarrhythmia discrimination module 315 again initiates storage of a segment of the sensed far-field signal. Instead of the IMD 300 performing the additional analysis to confirm the classification of the detected tachyarrhythmia, information is communicated to second device for the analysis.

For instance, if the additional analysis is morphology comparison, the stored segment is communicated to second device for comparison of a far-field signal morphology to a morphology template stored at the second device. The IMD 300 receives an indication whether the detected tachyarrhythmia is atrial tachyarrhythmia from the second device via the communication circuit 330. If the indication is a confirmation of atrial tachyarrhythmia, the classification may be used by the IMD 300 to begin an anti-tachyarrhythmia treatment or the IMB 300 may begin gathering the previously described statistics.

According to some examples, V-V pattern recognition is used to detect atrial tachyarrhythmia in the absence of dedicated atrial sensing circuitry. Alternating patterns of long and short V-V intervals can be recognized as being indicative of atrial tachyarrhythmia.

Figure 4:
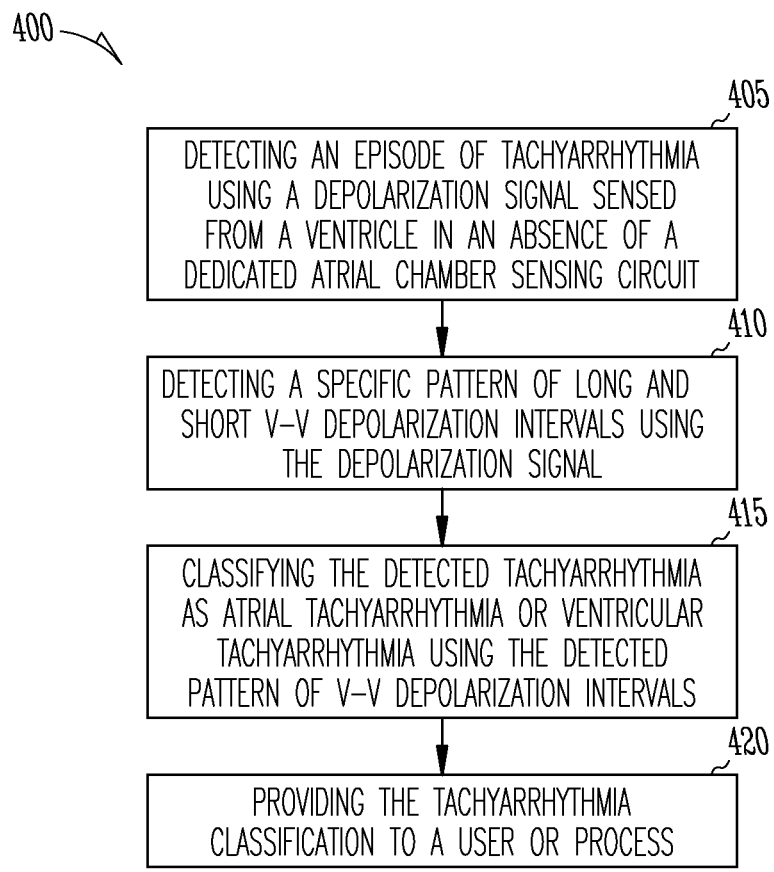
FIG. 4 is a flow diagram of an example of a method of detecting atrial tachyarrhythmia using an IMB that does not have dedicated atrial sensing circuits.

FIG. 4 is a flow diagram of an example of a method 400 of detecting atrial tachyarrhythmia using an IMB that does not have dedicated atrial sensing circuits. At block 405, an episode of tachyarrhythmia is detected using a device such as an IMB. The tachyarrhythmia is detected from a cardiac depolarization signal sensed from a ventricle using a dedicated implantable ventricular sensing circuit and in an absence of a dedicated atrial chamber sensing circuit. For example, the depolarization signal may be sensed using bipolar electrodes 120A and 120B and a sense amplifier as discussed above in regard to FIG. 1. In certain examples, the device senses cardiac depolarization signals and detects tachyarrhythmia by detecting a depolarization rate that exceeds a tachyarrhythmia detection rate threshold.

At block 410, a sudden presence of long and short V-V depolarization intervals is detected using the depolarization signal. The sudden presence of a characteristic pattern of short V-V intervals mixed with longer intervals may be an indication of an atrial tachyarrhythmia event such as AF. For example, the V-V intervals can have a pattern of "short-long-short-long, etc." This pattern can be used to identify AF, without dedicated atrial sensing.

Figure 5:
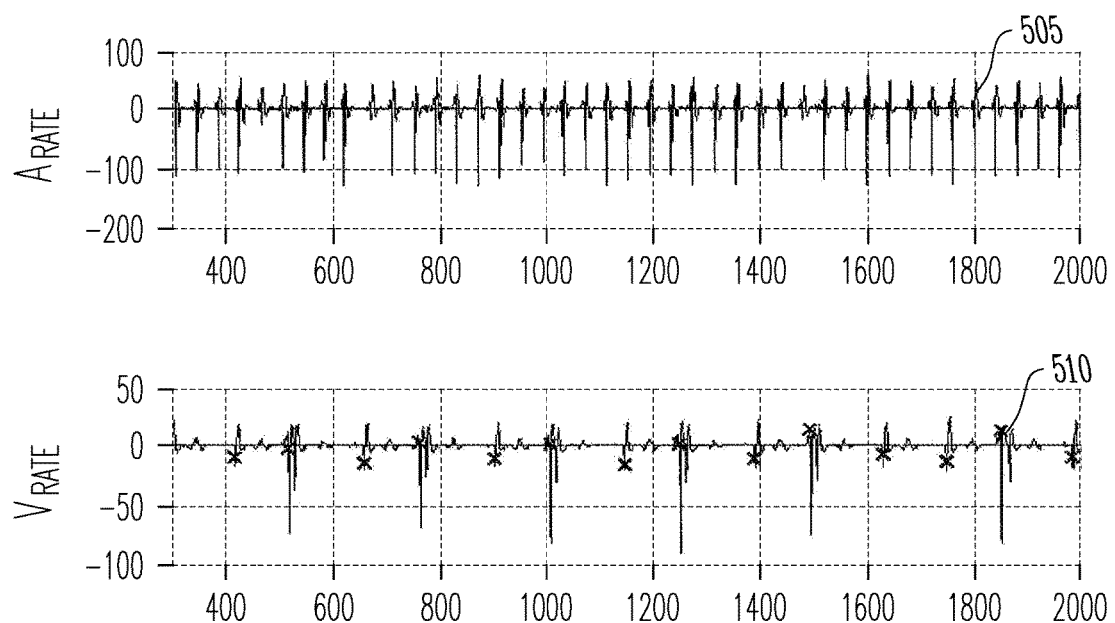
FIG. 5 shows an example of a characteristic pattern of V-V intervals during an AF episode.

FIG. 5 shows an example of a "short-long" pattern of the V-V intervals during an AF episode. The top trace 505 shows what a bipolar atrial electrogram sensed from the atrial lead would look like (if it were present) and the bottom trace 510 is a bipolar ventricular electrogram sensed from a ventricular lead (e.g., sensed with bipolar electrodes 120A and 120B on lead 115 in FIG. 1, these electrodes are sometimes referred to as a Vrate channel). The x-axis shows the data sample indices (using a sampling rate of 200 Hz). The crosses on the ventricular electrogram mark the ventricular events detected in the Vrate channel.

In some examples, an interval is a long interval if it is longer than a specified interval threshold, and an interval is a short interval if it is less than a specified interval threshold. One threshold may be used to identify long and short threshold. In FIG. 5, the V-V intervals in the data segment were (in milliseconds): 250, 347.5, 260, 350, 262.5, 350, 260, 345, 255, 340, . . . With a single threshold setting at, for example, 300 ms, the "short-long" pattern can be determined. In certain examples, a separate threshold is used to identify short thresholds and to identify long thresholds.

In some examples, a running average V-V interval is calculated. An interval is long if it exceeds the average V-V interval by a predetermined percentage, and an interval is short if it is less than the average V-V interval by a predetermined percentage. The short intervals mixed with long intervals is deemed to be sudden if a threshold number of mixed short and long intervals occur within a predetermined interval of time or within a specified number of V-V intervals.

At block 415, the detected tachyarrhythmia is classified as atrial tachyarrhythmia or ventricular tachyarrhythmia using a detected pattern of long and short V-V depolarization intervals. Using the example of FIG. 5, a captured repeated pattern of "short, long, short, long, . . . " may indicate AF. Thus, the detected tachyarrhythmia is classified according to a characteristic interval pattern recognized by the IMD. Other characteristic patterns may also be useful. At block 420, the tachyarrhythmia classification is provided to a user or process.

Returning to FIG. 3, to implement the method 400 the signal analyzer module 310 measures V-V intervals. The tachyarrhythmia discrimination module 315 detects an episode of tachyarrhythmia using the sensed depolarization signal using any of the methods described previously. The tachyarrhythmia discrimination module 315 detects a sudden presence of long and short V-V depolarization intervals and classifies the detected tachyarrhythmia as atrial tachyarrhythmia or ventricular tachyarrhythmia using a detected pattern of long and short V-V depolarization intervals. The specific pattern of long and short intervals may be a default pattern or may be programmed into the device by a clinician specifically for the subject. The tachyarrhythmia discrimination module 315 then provides the tachyarrhythmia classification to a user or process.

Once the detected tachyarrhythmia has been classified, in some examples the tachyarrhythmia discrimination module 315 uses further analysis to confirm the tachyarrhythmia. In certain examples, the tachyarrhythmia is confirmed by a morphology analysis using a sensed far-field signal as described herein.

In some examples, once the tachyarrhythmia is classified, the IMD 300 gathers statistics about the tachyarrhythmia. In certain examples, the tachyarrhythmia discrimination module 315 initiates storage of a segment of the sensed depolarization signal and initiates storage of a histogram of V-V depolarization intervals. The signal segment and the histogram are communicated to a second device.

As set forth previously, lack of atrial sensing makes it difficult for a clinician to retrospectively diagnose atrial tachyarrhythmia such as AF and AT, yet this information is often important to a physician or clinician. The several examples described herein provide for an IMD to automatically diagnose atrial tachyarrhythmia even though dedicated atrial chamber sensing circuit is absent in the device.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac signal sensing circuit, configured to provide a sensed depolarization signal from a ventricle;
   a processor communicatively coupled to the cardiac signal sensing circuit, the processor including:
      a signal analyzer module configured to measure V-V depolarization intervals; and
      a tachyarrhythmia discrimination module configured to:
         detect an episode of tachyarrhythmia using the measured V-V depolarization intervals;
         detect a sudden presence of a mix of both long and short V-V depolarization intervals;
         classify the detected tachyarrhythmia as atrial tachyarrhythmia or ventricular tachyarrhythmia using a detected pattern of long and short V-V depolarization intervals included in the mix of both long and short V-V depolarization intervals; and
         provide the tachyarrhythmia classification to a user or process.

2. The apparatus of claim 1, including:
   a memory communicatively coupled to the processor and configured to a store a signal morphology template; and
   a far-field sensing channel configured to provide a far-field atrial and ventricular signal using an electrode location that is outside of an atrium or ventricle, and wherein the tachyarrhythmia discrimination module is configured to:
upon classifying the detected tachyarrhythmia as atrial tachyarrhythmia, initiate sensing of the far-field signal; and
initiate a comparison a morphology of the far-field signal to a stored morphology template by the signal analyzer module; and
confirm the classification as atrial tachyarrhythmia using the morphology comparison.

3. The apparatus of claim 2, wherein the signal analyzer module is configured to:
calculate a measure of similarity between a segment of the far-field signal and the morphology template, wherein the stored morphology template is representative of normal sinus rhythm;
calculate a central tendency of the measure of similarity and a variance of the measure of similarity, and
wherein the tachyarrhythmia discrimination module is configured to confirm the classification as atrial tachyarrhythmia when the central tendency of the measure of similarity is above a central tendency threshold, the variance of the measure of similarity is within a variance range, and the depolarization rate or interval satisfies a rate or interval detection threshold.

4. The apparatus of claim 1, including:
a memory communicatively coupled to the processor; and
a communication circuit, communicatively coupled to the processor, configured to communicate information wirelessly with a second separate device, and
wherein the tachyarrhythmia discrimination module is configured to:
upon classifying the detected tachyarrhythmia as atrial tachyarrhythmia, initiate storage of a segment of the depolarization signal when a duration of the detected arrhythmia exceeds a duration threshold;
initiate storage of a histogram of V-V depolarization intervals, wherein the histogram indicates regular and irregular V-V depolarization intervals; and
communicate the stored segment and histogram from an implantable medical device to a second device.

5. A method comprising:
detecting an episode of tachyarrhythmia using a depolarization signal sensed from a ventricle in an absence of a dedicated atrial chamber sensing circuit;
detecting a sudden presence of a mix of both long and short V-V depolarization intervals using the depolarization signal;
classifying the detected tachyarrhythmia as atrial tachyarrhythmia or ventricular tachyarrhythmia using a detected pattern of long and short V-V depolarization intervals included in the mix of both long and short V-V depolarization intervals; and
providing the tachyarrhythmia classification to a user or process.

6. The method of claim 5, including:
upon classifying the detected tachyarrhythmia as atrial tachyarrhythmia, sensing a second signal using a far-field sensing channel; and
comparing a morphology of the second sensed signal to a morphology template, and
wherein classifying the tachyarrhythmia includes confirming the classification as atrial tachyarrhythmia using the morphology comparison.

7. The method of claim 6, including:
calculating a measure of similarity between a segment of the far-field signal and the morphology template, wherein the stored morphology template is representative of normal sinus rhythm;
calculating a central tendency of the measure of similarity and a variance of the measure of similarity, and
confirming the classification as atrial tachyarrhythmia when the central tendency of the measure of similarity is above a central tendency threshold, the variance of the measure of similarity is within a variance range, and the depolarization rate or interval satisfies a rate or interval detection threshold.

8. The method of claim 5, including:
detecting that the episode of tachyarrhythmia is an episode of atrial fibrillation (AF) using the depolarization signal;
determining a duration that the subject spends in AF when classifying the detected tachyarrhythmia as atrial tachyarrhythmia; and
calculating a value of AF burden using the duration that the subject spends in AF.

9. The method of claim 5, including
upon classifying the detected tachyarrhythmia as atrial tachyarrhythmia, storing a segment of the depolarization signal when a duration of the detected arrhythmia exceeds a duration threshold;
storing a histogram of V-V depolarization intervals, wherein the histogram indicates regular and irregular V-V depolarization intervals; and
communicating the stored segment and histogram from an implantable medical device to a second device.

10. The apparatus of claim 1, wherein the tachyarrhythmia discrimination module is configured to:
detect an episode of atrial fibrillation (AF) using the depolarization signal;
determine a duration that the subject spends in AF; and
calculate a value of AF burden using the duration that the subject spends in AF.

11. The apparatus of claim 10, wherein the tachyarrhythmia discrimination module is configured to generate AF histogram data and communicate the histogram data to a separate device.

12. The method of claim 8, wherein the tachyarrhythmia discrimination module is configured to generate AF histogram data and communicate the histogram data to a separate device.

* * * * *